United States Patent

Tapia et al.

[11] Patent Number: 5,964,767
[45] Date of Patent: Oct. 12, 1999

[54] HOLLOW SEALABLE DEVICE FOR TEMPORARY OR PERMANENT SURGICAL PLACEMENT THROUGH A BONE TO PROVIDE A PASSAGEWAY INTO A CAVITY OR INTERNAL ANATOMIC SITE IN A MAMMAL

[76] Inventors: Eduardo Armando Tapia; Estela María Perez de Tapia, both of Virrey Olaguer y Feliú 2970 6th Floor "B", (1426) Buenos Aires; Mario Emilio Zernotti, Extremadura 2389, (5014) Barrio Maipú Province of Cordoba; Luis Antonio de Zavaleta, Malabia 2166, 6th Floor "A", (1425) Buenos Aires, all of Argentina

[21] Appl. No.: 08/928,134
[22] Filed: Sep. 12, 1997
[51] Int. Cl.⁶ .................................................. A61B 17/56
[52] U.S. Cl. .............................................. 606/73; 411/177
[58] Field of Search ............................... 606/73, 72, 232, 606/76, 77; 604/174, 179, 177, 263, 167; 411/384, 383, 178, 177, 179, 396, 397, 432, 163, 353, 366

[56] References Cited

U.S. PATENT DOCUMENTS

| | | | |
|---|---|---|---|
| 4,145,764 | 3/1979 | Suzuki et al. | 606/76 |
| 4,484,570 | 11/1984 | Sutter et al. | 606/72 |
| 4,647,883 | 3/1987 | Oxley | 411/366 |
| 4,822,223 | 4/1989 | Williams | 411/178 |
| 5,037,259 | 8/1991 | Duran et al. | 411/177 |
| 5,584,629 | 12/1996 | Bailey et al. | 411/178 |
| 5,711,763 | 1/1998 | Nonami et al. | 606/76 |

*Primary Examiner*—Michael Buiz
*Assistant Examiner*—Julian W. Woo
*Attorney, Agent, or Firm*—Evenson, McKeown, Edwards, Lenahan, P.L.L.C.

[57] ABSTRACT

The present invention refers to a sealable device for temporary or permanent surgical placement through a bone to provide a passage into a cavity or internal anatomic site in a mammal. The sealable device comprises two preferred embodiments: in the first one the device comprises two members, the first one provides a passage through the bone, and the second one, which is movable, is used as a stopper means for the first member, and in the second embodiment, a third removable member is added, which may be connected with said second end of said first member so that the device is affixed to the bone it runs through. The device can be used, for example, for diagnostic purposes, for topical in situ therapy, of medical treatment or for viewing into the cavity. The cavity may be, for instance, the sinus maxillaris. If so, the temporary or permanent placement of the device is carried out via the canine fossa or the lower meatus.

8 Claims, 2 Drawing Sheets

HOLLOW SEALABLE DEVICE FOR TEMPORARY OR PERMANENT SURGICAL PLACEMENT THROUGH A BONE TO PROVIDE A PASSAGEWAY INTO A CAVITY OR INTERNAL ANATOMIC SITE IN A MAMMAL

FIELD OF THE INVENTION

The present invention relates to a hollow sealable device for temporary or permanent surgical placement through a bone to provide a passage into a cavity or internal anatomic site in a mammal.

BACKGROUND OF THE INVENTION

Problems associated with acute or chronic diseases in cavities or internal anatomical sites in the body, for which it is sometimes necessary to enter via a bone are known in medicine. The sinus maxillaris is an example of a cavity where much too often rhinosinus diseases occur, which require medical and/or surgical treatment. The problem, in these cases, is the passage into the cavity, either for diagnostic purposes, or for topical treatment in situ, as well as medical treatment, or observation and evaluation.

There are known in current medicine certain devices for temporary insertion related to sinus cavities.

Using "SinoJet™" from ATOS MEDICAL company, it is possible to insert a silicone rubber tube via the lower meatus. Its insertion is carried out by a special puncturing or driving means, similar to a trigger. Insertion is fast, by pressing on and breaking tissues. Therefor, the only feasible path for this device is the lower meatus. While this tube may be inserted under a certain degree of control, the possibility that it be introduced too deep into the sinus maxillaris, thus causing undesired effects, cannot be ruled out. The tube may be kept in place for a few days as a means to be in contact with the sinus maxillaris in the lower meatus, but it is not designed or intended to be inserted permanently or for long periods of time and it is not sealable. At its forward end, the tube is in the shape of a truncated arrow with a pair of fins on either side, and its rear end is beadless. This tube allows for irrigation or flushing of the sinus maxillaris, but because of its small inner diameter it is impossible to look into the sinus maxillaris, since it does not allow for insertion of any direct vision optical instrument through it.

"Rains Frontal Sinus Stent™", sold by Smith+Nephew ENT, is a silicone rubber device designed solely for temporary insertion into de frontal sinus. Following frontal sinus endoscopic surgery, the tube is inserted exclusively for the purpose of preventing a surgical complication or natural reclosure of the opening in the frontal recess. The tube will maintain a surgical opening cut through the ostrum of the frontal sinus for 7 to 14 dais after surgery. The device has a hollow stem, and at its forward end it is provided with a head or bulb which, upon insertion into the frontal sinus, it keeps the tube within the cavity. While it is supposed to be self-fastening, it does not allow for an accurate control of its advancing or keeping the tube in place within the frontal sinus. This device is not designed for permanent placement, it is not sealable, it cannot be used to inject or remove any solutions from the frontal sinus nor does it allow for insertion of direct viewing optical instruments through its lumen.

"Shikani Middle Meatal Antrostomy Stent (SMMAS)™" sold by Micromedics, Inc., is designed to be inserted following functional endoscopic surgery of the sinus maxillaris. The above device, SMMAS, is introduced via an antrostomy made in the middle meatus, by means of a Ferris-Smith forceps. The device is kept in place temporarily for 10 to 14 days after surgery, after which it is readily removed via the nasal fossa. It has a sole purpose: preventing adhesions from being formed by adjacent tissues through connection of same between the middle ethmothurbinate and the nasal side wall. The above device is made of a soft material, such as silicone rubber, it has two fins at its forward end which prevent the device from undesirably slipping out of the opening, and at its rear end it has a bead that prevents both the middle ethmothurbinate and the nasal side wall from attaching one another, and the undesirable advance of the device into the cavity of the sinus maxillaris. The device SMMAS is not sealable and its use is intended for a short period of time, with insertion only through the middle meatus.

There are known, in prosthetic and implant medicine devices to be affixed to a bone. These devices generally comprise one or several components, for a reliable attachment of the same to the bone, because prostheses attached to a bone will generally have to bear a heavy load, whether it is a prosthesis or a dental implant, a lockscrew in a limb, an artificial joint or the like. Therefore, it is required a reliable attachment, which provides for an unlimited and more secure use of the prosthesis. The components are substantially solid, and they may be generally attached to a bone by means of threads, since this combination insures a better attachment.

Generally, devices are solid or partially hollow. The latter may be provided with a stopper system, but they cannot provide a passageway through their lumen between two different anatomical sites, for one of their ends is closed.

There are also hollow devices which, after being inserted through a bone, define a passageway between two different anatomical sites, but which lack an internal stopper system, leaving both of the above histic surfaces in permanent open connection.

SUMMARY OF THE INVENTION

None of the existing devices are provided, in their designs, with the two structures put together in the present invention:

1) A rigid device substantially in the shape of a hollow tube with both ends open.
2) The stopper means for the selective opening or closure of the inner passage of the present device.

Therefore, it is an object of the present invention to provide a sealable device for temporary or permanent placement through a bone to provide a passage into a cavity or internal anatomic site in a mammal, which allows to enter said cavity or internal anatomic site, both for diagnostic purposes and for topical in situ therapy, as well as medical and/or surgical treatment or observation.

Another object of this invention is to provide a device which may be applied to any cavity or internal anatomic site whatsoever, through any bone in any mammal. For example, in the case of the sinus maxillaris the instant device may be inserted as much via the canine fossa as via the lower meatus, thus connecting an easily reached endobucal or endonasal exogenous compartment, with an endogenous sinusomaxillary compartment.

A further object of the invention is to provide a simple device, which allows for a reliable attachment to the bone, inasmuch as there is no heavy load imposed on it.

In a preferred embodiment, the device comprises two members: the first one provides the passage through the bone, and the second one, which is movable, is used as a stopper means for the first member.

In another preferred embodiment the device comprises three members; the first member provides the passage through the bone, the second one, which is movable, is used as a stopper means for the first member, and the third member is removable and may be connected with said second end of said first member in order to affix the device to the bone the device has been inserted through.

The following configurations of the first and second members are variations of the above preferred embodiments.

In a preferred embodiment, the first member comprises a substantially cylindrical body, and it has an internal passage which runs longitudinally through it. The passage has an inner diameter that allows for insertion of an optical instrument for viewing the inner side of the cavity, for the removal of materials from the cavity for diagnostic purposes, for the introduction of materials for therapeutic purposes or for medical and/or surgical treatment.

The second member is in a shape that is complementary to the inner passage of the first member for the purpose of sealing the passage when said member is inserted in it.

The device is made of a biocompatible material, such as surgical titanium or stainless steel or alloys of the same, but any other biocompatible material may be used. At least one of the three members may be made of a biocompatible material different from that of the other two members, or all three members may be made of different biocompatible materials. The two or three members may be coated with biocompatible materials different from the ones the bodies of said members are made of.

The first member may be affixed to the bone it is inserted through in various ways, therefore, it includes one or more fastening means on its outer side, and/or at one or both rear and forward ends.

The fastening means on the outer side may be a thread whereby the first member is affixed to the bone.

The forward end of the first member may be provided with a flange, as a retaining means, which surrounds the external edge of the forward end of the first member and the outer edge of which protrudes from the surface of the body of the first member. Upon inserting the first member through the bone, the flange holds the bone and prevents the member from slipping further into the cavity.

On the outer end, the fastening means may be a substantially rectangular fin affixed from within the internal cavity.

The first member further comprises at least one coupling means for connection with the second member.

In a preferred embodiment, the second movable member is removable and it can be fastened by means of a thread provided on the inner side of the first member, which cooperates with a thread provided on the outer side of the second member.

In another preferred embodiment, the second member is not removable, but it is coupled with the first member by a lock.

In order to achieve a better sealing effect, the second member may be provided, in a further preferred embodiment, with a head at its forward end, which may be used as a screw head, and it may be in any shape that is convenient for using any conventional screwdriver. In addition, the head may be ceramic-coated.

The third member, which is only included in the third embodiment of the present invention, has an outer side of hexagonal or octagonal shape. The inner side of said third member is round and it may be provided with a thread in a preferred embodiment. In a preferred embodiment the third member is a nut.

BRIEF DESCRIPTION OF THE DRAWINGS

The above objects are achieved by the device of this invention, which is further illustrated in the following figures, wherein.

DETAILED DESCRIPTION OF THE INVENTION

Figure 1:
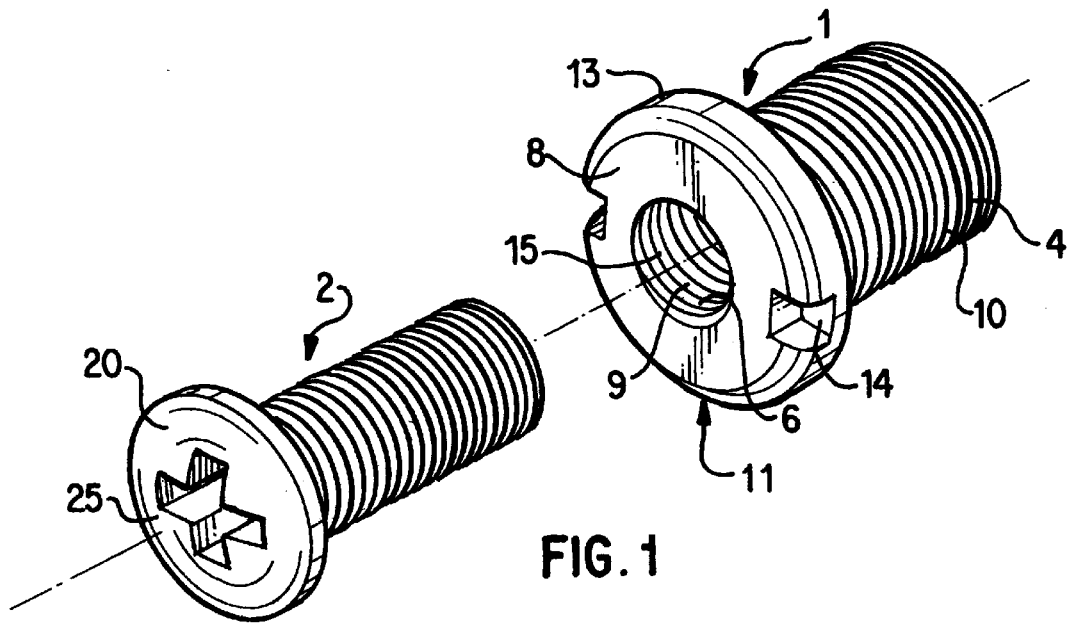
FIG. 1 is a perspective exploded view of a first embodiment of the sealable device of the present invention.
Figure 2A:
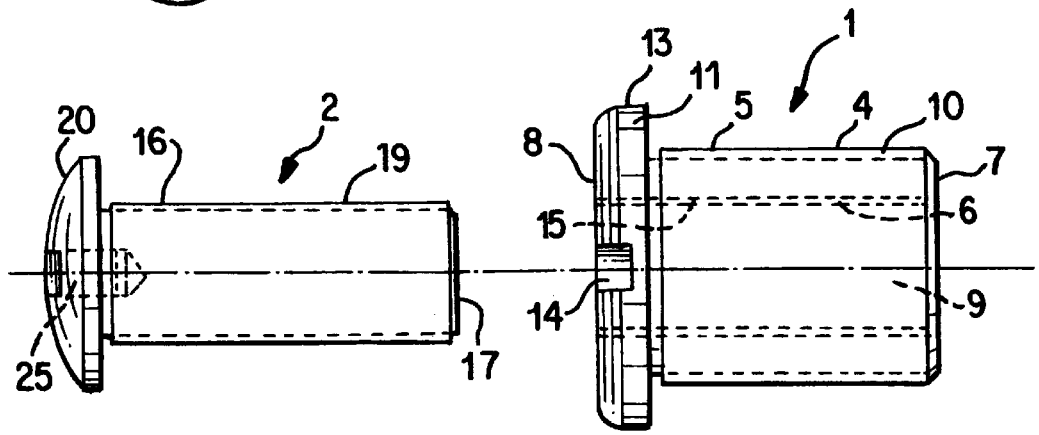
FIG. 2A is a side view of the first embodiment of the sealable device of the present invention.

As shown FIGS. 1 and 2A, in a first embodiment, the sealable device for temporary or permanent placement through a bone to provide a passageway into an internal cavity in a mammal comprises two members, 1 and 2.

In another preferred embodiment (FIG. 3) the sealable device of the present invention comprises three members, 1, 2 and 3.

The object of this invention is the temporary or permanent placement of the sealable device through a bone to provide a passageway into an internal cavity in a mammal. Therefor, all the members 1, 2 and 3 of the device are made of a biocompatible material. When placement of the device is to be permanent, the preferred biocompatible material is surgical titanium or a surgical titanium alloy, but it can also be any other biocompatible material. All two 1,2 or three members 1, 2, 3 may be made of the same biocompatible material, or one of the members 1, 2, or 3 may be made of a biocompatible material different from the others, or each of the members 1, 2, 3 may be made of different biocompatible materials. Whether or not the bodies of all three members 1, 2, 3 are made of different biocompatible materials, their surfaces may be coated with another biocompatible material, which may be the same in all three members, or different for one or more of the members.

The first member 1 may be designed according to several preferred embodiments, some of which are shown in FIGS. 2A, 2B, 4A and 4B.

The first member 1 is hollow and it generally comprises a body 4 of a substantially cylindrical shape. This hollow member has an outer side 5, an inner side 6, two ends 7, 8, of which the rear first end 7 enters the internal cavity in the mammal and the second forward end 8 is approachable from outside, with said first member defining an inner passage 9 which runs longitudinally through it.

In order to be affixed to the bone through which the device is introduced, the first member 1 comprises one or more fastening members 10, 11, 12, which may be located on the outer side 5, at the first rear end 7 or at the second forward end 8.

Figure 4A:
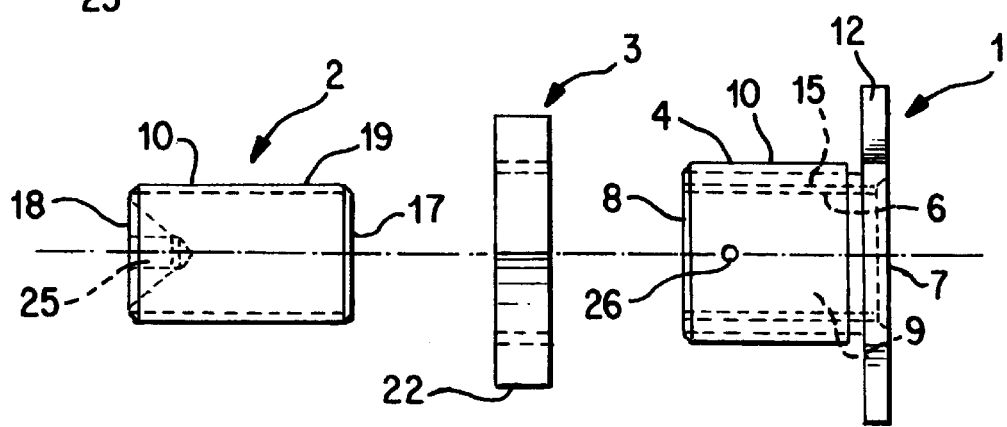
FIG. 4A is a side view of a second embodiment of the sealable device of the present invention.
Figure 4C:
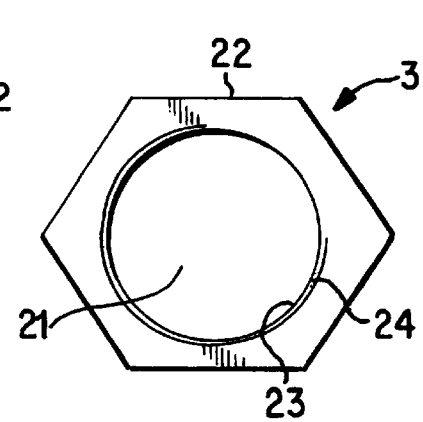
FIG. 4C is a front view of the forward end of the second member of the sealable device.
Figure 4D:
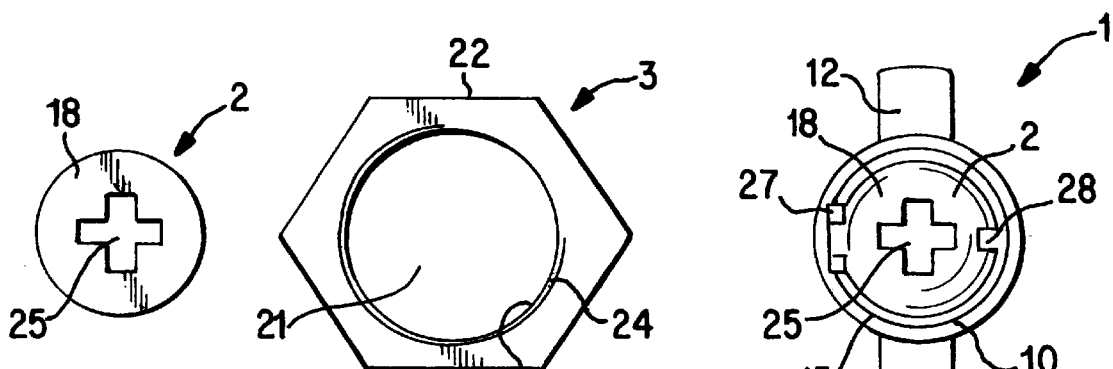
FIG. 4D is a front view of the forward end of the third member of the sealable device.
Figure 4B:
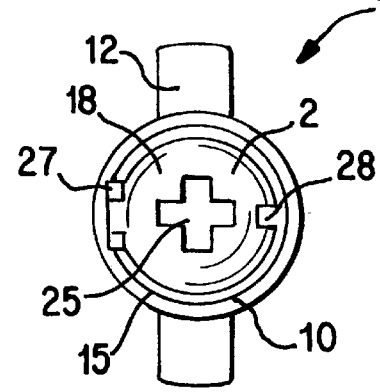
FIG. 4B is a front view of the forward end of the first member of the sealable device.

The fastening means 10 on the outer side 5 is an external thread 10, which is screwed into the bone, thereby attaching the device to the bone (FIGS. 2A, 4A and 4B).

The fastening means 11 at the forward end 8 of the first member is a outward radially extending flange 11, the external edge 13 of which protrudes from the outer side 5 of the body 4 of the first member 1. The flange 11 may be of round, square, hexagonal, octagonal shape or the like. The exterior edge 13 of the flange may be provided with two oppositely arranged notches 14 for the purpose of inserting a clamp which is useful, for example, to hold the first member 1 in place when inserting or removing the second member 2. In order to affix the instant sealable device, the flange 11 is anchored to the side of the pierced bone facing the outside of the mammal.

The fastening means 12 at the first rear end 7 of the first member 1 is a fin 12 provided at the rear end of said first member 1. The fin 12 is preferably of a rectangular shape, but it can also be of an oval shape or any other shape which allows for insertion of the first member 1 through the hole provided for that purpose. The present sealable device is attached by the anchorage of the fin 12 onto the side of the bone facing into the internal cavity in the mammal. By the above fin 12, the first member 1 is prevented form being undesirably released from the internal cavity in the mammal.

Where the fastening means 12 is provided at the first forward end 7, the body of the first member 1 has at least two holes 26 through the peripheral wall, substantially opposite one another, which are used to fasten the first member 1 during its insertion into the bone, e.g., by means of a thread, after inserting the first rear end 7 with the fin 12 into the internal cavity in the mammal.

The first member 1 has at least one of these fastening means 10, 11, 12, but, depending on its intended application, there are certain embodiments which include two or three fastening means 10, 11, 12.

In order to connect the second member 2, the first member 1 comprises one or more coupling means 15 which may be located on the inner side 6 or at the second forward end 8.

The coupling means 15 on the inner side 6 consists of an internal thread 15, which cooperates with another thread, which may be provided on the outer side 16 of the body of the second member 2, to connect and seal the first member 1 with the second member 2. In embodiments wherein the first member 1 does not have an internal thread 15, the inner side 6 of the same is smooth.

In a preferred embodiment, the coupling means at the forward end 8 of the first member 1 is a lock 27 (FIGS. 2B and 4B) whereby the second member 2 is coupled with the first member 1. In this preferred embodiment, the first member 1 may have a closure means 28 (FIGS. 2B and 4B) to secure the second member 2, thus insuring a maximum sealing of the device when it is in a closed state.

The sealable device comprises a second movable member 2 which has an outer side 16 and two ends, a first forward end 17 and a second rear end 18. The second movable member 2 is removable when it is not coupled with the first member 1 by the lock 27.

The second member 2 has a cross section and an outer diameter that match the cross section and an outer diameter of the internal passage 9 of the first member 1, allowing the second member 2 to seal the internal passage 9 of the first member 1 when the latter is inserted into the first member. The body of the second member 2 may have a length equal or greater than the length of the first member 1, or much less than the same, in case the second member 2 is attached to the first member 1 by a hinge. Generally, the cross section of the body of the second member 2 has a round shape or the like. The inner side 16 of said second member 2 may be smooth or it may be provided with an internal thread 19.

Figure 2C:
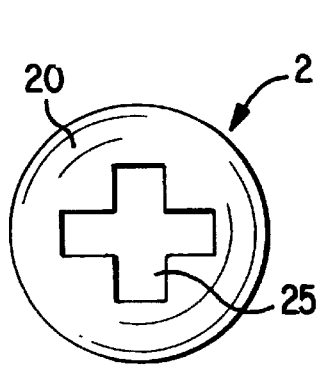
FIG. 2C is a front view of the forward end of the second member of the sealable device.
Figure 2B:
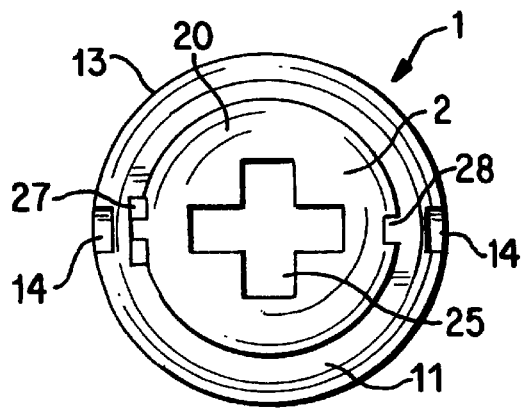
FIG. 2B is a front view of the forward end of the first member of the sealable device.

In several preferred embodiments, the second member 2 has a screw head 20 at the second, forward end 18 (see FIGS. 1, 2A and 2C) which may be ceramic-coated.

Figure 3:
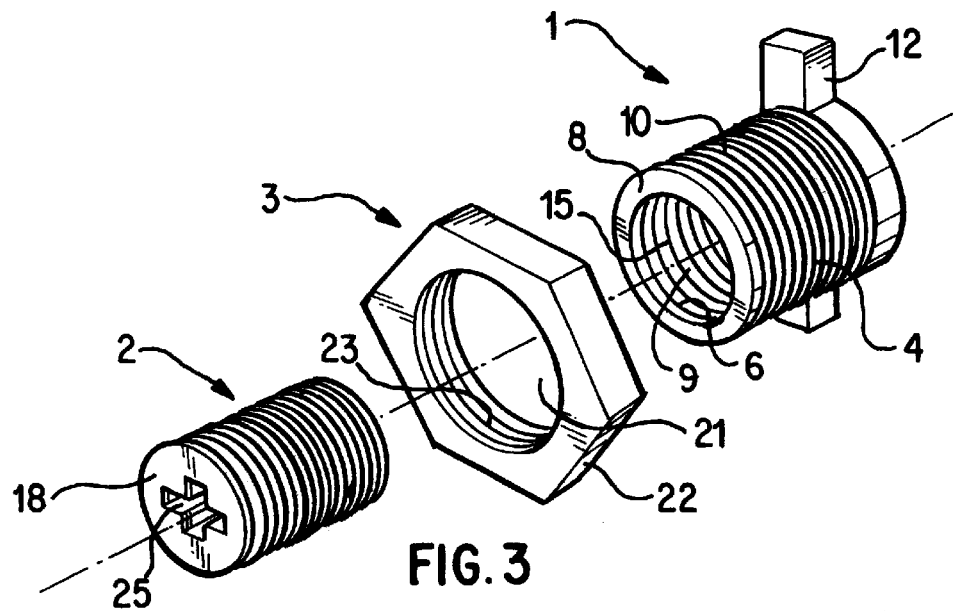
FIG. 3 is a perspective exploded view of a second embodiment of the sealable device of the present invention.

In further embodiments, the second, forward end 18 of the second member 2 does not have a screw head. (FIGS. 3 and 4C).

However, in certain preferred embodiments, the second, forward end 18 of the second member 2 is provided with an opening 25 to insert a screwdriver therethrough (FIGS. 1, 2C, 3 and 4C). This opening 25 may be suitable for any type of screwdriver.

In FIG. 4A there is shown that the sealable device for temporary or permanent surgical placement through a bone to provide a passage into a cavity or internal anatomic site in a mammal can include a third removable member 3, which may be connected with said second end 8 of said first member 1, and has a central hole 21, an outer side 22 and an inner side 23.

The third member 3 is usually a nut (FIGS. 4A and 4D). The outer side 22 of the third member 3 may have an hexagonal, octagonal, rectangular, circular shape or the like. The inner side 23 of said third member 3 is substantially circular, and may be provided with a thread 24, whereby the third member 3 is affixed to the second, forward end 8 of the first member 1 through the external thread 10 on the outer side 5 of the first member 1 to prevent the first member 1 to advance into the internal cavity in a mammal.

In case the second, forward end 8 of the first member 1 is provided with a flange 11, the body of the first member 1 protrudes forward from the flange 11, to allow the third member 3 to be fastened onto the extending external thread 10.

In the embodiments of the sealable device which employ a third member 3, the various embodiments disclosed for the first and second members 1, 2 can also be applied.

The use of the present invention will be further understood in connection with an example of how to provide a passageway into the sinus maxillaris.

In the case of the sinus maxillaris, insertion of the sealable device may be carried out from two different approaches:

1) via the canine fossa: an incision is made with the scalpel up to the mucoperiosteum. The anterior wall of the sinus maxillaris is taken apart and hemostasis is effected. Thereafter, an opening is made (sinusotomy) by means of a cool-cutter and micromotor, until the sinus lumen is encountered. The device is then inserted: a slight pressure is exerted on the bone and the device in screwed into the thickness of the maxilla. Once it has been introduced, it is fastened onto the wall and, if necessary, the lips of the incision may be sutured. Thereafter a clamp is inserted to hold the external jacket of the device (first member), the internal stopper (second member) is unscrewed and the correct fastening of the device is verified.

2) Via the lower meatus: the luxation of the lower to middle ethmoturbinate is first conducted, to achieve a good view of the lower meatus. A meatotomy is then carried out by means of a trocar or cutter with an angle bar (micromotor). Because of bleeding, a previous incision is not advisable in this approach. Thereafter, the device is inserted as in the above route, but with angular tools for work inside the nasal fossa.

After the sealable device has been inserted through the canine fossa or the lower meatus, a sealable passage into the sinus maxillaris is achieved. This passage renders it possible to make diagnoses, topical in situ treatments, medical treatments or observations through an optical instrument to be inserted. When the passage is not designed for one of the above actions, the first member, which provides the passage into the internal cavity in a mammal, is sealed by the second member.

We claim:

1. A method for forming a temporary or permanent, unobstructed passageway through a bone into an internal cavity or anatomic site in a mammal, comprising the steps of:

forming a passageway through a bone or other tissue into an internal cavity or anatomic site;

inserting a hollow first member having a first end and a second end, said first member being open only at said first and second ends, within said passageway thereby forming an unobstructed passage to the cavity or anatomic site wherein said second end is positioned to be accessed from outside the cavity or site;

fixing said hollow first member to the bone; and removably sealing said second end with a second member which is adapted to be connected with said first hollow member by a coupling means.

2. A hollow sealable device for temporary or permanent surgical placement insertable through a bone to provide a passageway into an internal cavity or anatomic site in a mammal, said device being made of a biocompatible material and comprises a first hollow member that has an outer side and an inner side, a first, rear end which is insertable in the cavity and a second, forward end which is accessible from outside the cavity; said hollow member being provided with openings only at said first and second ends thereby defining and maintaining an interior passage which spans it longitudinally; wherein said passage has a minimum interior diameter so that an instrument way be inserted into the cavity; said first member having at least one fastening means on its outer side, at said first rear end or at said second forward end, for the purposes of keeping said first member temporarily or permanently affixed to a bone and preventing the first member from undesirably advancing or slipping out; said device further comprising a second movable member that has an outer side and two ends, a first rear end and a second, forward end, said second member being connected to the first member by a coupling means provided on the inner side or at the second, forward end of the first member; said second member sealing said passage in said first member; wherein said second member has a screw head being provided with a ceramic coating.

3. A hollow sealable device for temporary or permanent surgical placement, insertable through a bone to provide a passageway into an internal cavity or anatomic site in a mammal, said device being made of a biocompatible material and comprises a first hollow member that has an outer side and an inner side, a first, rear end which is insertable in the cavity and a second, forward end which is accessible from outside the cavity; said hollow member being provided with openings only at said first and second ends thereby defining and maintaining an interior passage which spans it longitudinally; wherein said passage has a minimum interior diameter so that an instrument may be inserted into the cavity; said first member having at least one fastening means on its outer side, at said first rear end or at said second forward end, for the purposes of keeping said first member temporarily or permanently affixed to a bone and preventing the first member from undesirably advancing or slipping out; said device further comprising a second movable member that has an outer side and two ends, a first rear and a second, forward end, said second member being connected to the first member by a coupling means provided on the inner side or at the second, forward end of the first member; said second member sealing said passage in said first member; wherein said coupling means is a lock provided at said forward end of said first member, whereby said second movable member is connected with the forward end of the first member.

4. The device of claim 3, wherein said forward end of said first member is provided with a closure means to keep said passage in said first member sealed when the second member is coupled to the first member.

5. A hollow sealable device for temporary or permanent surgical placement, adapted to be inserted through a bone to provide a passageway into an internal cavity or anatomic site in a mammal, said device being made of a biocompatible material and comprising:

a first hollow member that has an outer side and an inner side, a first, rear end which is insertable in the cavity and a second, forward end which is accessible from outside the cavity; said hollow member being provided with openings only at said first and second ends thereby defining and maintaining an interior passage which spans it longitudinally; wherein said passageway has a minimum interior diameter so that an instrument may be inserted into the cavity; said first member having at least one fastening means on its outer side, at said first rear end or at said second forward end, for the purposes of keeping said first member temporarily or permanently affixed to a bone and preventing the first member from undesirably advancing or slipping out; and a second movable member that has an outer side and two ends, a first rear end and a second, forward end, said second member being connected to the first member by a coupling means provided on the inner side or at the second, forward end of the first member; said second member sealing said passage in said first member; wherein at least one of said fastening means is a substantially rectangular fin provided at the first, rear end of said first member, which may be anchored from the interior the cavity; and said first member comprising at least two holes, substantially opposite one another, which connect the outer side with the inner side of said first member.

6. The device of claim 5, wherein said second member has a screw head being provided with a ceramic coating.

7. The device of claim 6, wherein said coupling means is a lock provided at said forward end of said first member, whereby said second movable member is connected with the forward end of the first member.

8. The device of claim 7, wherein said forward end of said first member is provided with a closure means to keep said passage in said first member scaled when the second member is coupled to the first member.

* * * * *